(12) United States Patent
Samzelius

(10) Patent No.: US 6,837,241 B2
(45) Date of Patent: Jan. 4, 2005

(54) METHOD FOR ADAPTIVE TRIGGERING OF A BREATHING DEVICE, AND BREATHING DEVICE WITH ADAPTIVE TRIGGERING

(75) Inventor: Roger Samzelius, Vëllingby (SE)

(73) Assignee: Maquet Critical Care AB, Solna (SE)

( * ) Notice: Subject to any disclaimer, the term of this patent is extended or adjusted under 35 U.S.C. 154(b) by 99 days.

(21) Appl. No.: 09/982,700

(22) Filed: Oct. 18, 2001

(65) Prior Publication Data
US 2002/0056454 A1 May 16, 2002

(30) Foreign Application Priority Data
Nov. 13, 2000 (SE) .............................................. 0004141

(51) Int. Cl.⁷ .............................................. A61M 16/00
(52) U.S. Cl. .............................. 128/204.21; 128/204.18
(58) Field of Search ....................... 128/200.24, 204.18, 128/204.21, 204.22, 204.23, 202.16, 207.14, 207.15; 607/2, 3, 20, 42, 212

(56) References Cited

U.S. PATENT DOCUMENTS

| | | | |
|---|---|---|---|
| 4,050,458 A | | 9/1977 | Friend |
| 4,671,297 A | * | 6/1987 | Schulze, Jr. ................. 600/529 |
| 4,827,935 A | * | 5/1989 | Geddes et al. ................ 607/42 |
| 4,960,133 A | * | 10/1990 | Hewson .................. 128/207.15 |
| 4,972,842 A | * | 11/1990 | Korten et al. ............... 600/529 |
| 5,161,525 A | * | 11/1992 | Kimm et al. ........... 128/204.26 |
| 5,353,788 A | | 10/1994 | Miles |
| 5,373,842 A | * | 12/1994 | Olsson et al. ........... 128/204.21 |
| 5,390,666 A | * | 2/1995 | Kimm et al. ........... 128/204.26 |
| 5,513,631 A | | 5/1996 | McWilliams |
| 5,582,574 A | * | 12/1996 | Cramer ......................... 600/21 |
| 5,584,290 A | * | 12/1996 | Brain ..................... 128/207.15 |
| 5,660,171 A | * | 8/1997 | Kimm et al. ........... 128/204.23 |
| 5,671,752 A | * | 9/1997 | Sinderby et al. ....... 128/204.23 |
| 5,785,051 A | * | 7/1998 | Lipscher et al. ........ 128/207.15 |
| 5,820,560 A | * | 10/1998 | Sinderby et al. ............. 600/546 |
| 6,224,562 B1 | * | 5/2001 | Lurie et al. .................... 601/41 |
| 6,357,438 B1 | * | 3/2002 | Hansen .................. 128/204.18 |
| 6,360,740 B1 | * | 3/2002 | Ward et al. ............. 128/200.24 |
| 6,406,426 B1 | * | 6/2002 | Reuss et al. ................. 600/300 |
| 6,584,347 B1 | * | 6/2003 | Sinderby ..................... 600/546 |
| 6,588,423 B1 | * | 7/2003 | Sinderby ............... 128/204.23 |
| 6,597,939 B1 | * | 7/2003 | Lampotang et al. ......... 600/427 |
| 6,651,652 B1 | * | 11/2003 | Ward ..................... 128/200.24 |

FOREIGN PATENT DOCUMENTS

| | | |
|---|---|---|
| EP | 0 324 275 | 7/1989 |
| EP | 0 459 647 | 12/1991 |
| WO | WO 98/41146 | 9/1998 |
| WO | WO 99/43374 | 9/1999 |
| WO | WO 00/00245 | 1/2000 |

* cited by examiner

Primary Examiner—Henry Bennett
Assistant Examiner—Teena Mitchell
(74) Attorney, Agent, or Firm—Schiff Hardin LLP

(57) ABSTRACT

In a method for adaptive triggering of respiratory phases in a breathing device, and a breathing device operating according to the method, first respiration indicator signal is determined based on at least one of the parameters flow and pressure, the respiration indicator signal is compared with a trigger requirement and a trigger signal is generated when the respiration indicator signal fulfils the trigger requirement. In order to shorten response times to respiration changes without losing stability, an excitable cell signal related to respiration is measured, and a second respiration indicator signal is determined based on the measured excitable cell signal, and the trigger requirement is adapted in relation to the second respiration indicator signal.

15 Claims, 2 Drawing Sheets

METHOD FOR ADAPTIVE TRIGGERING OF A BREATHING DEVICE, AND BREATHING DEVICE WITH ADAPTIVE TRIGGERING

BACKGROUND OF THE INVENTION

1. Field of the Invention

The present invention relates to a method for adaptive triggering of A breathing device as well as to a breathing device operating according to the method.

2. Description of the Prior Art

"Triggering" as used herein means the activation of any respiration phase, i.e. both inspiration phases and expiration phases. This is a broader meaning than that normally understood by the term (triggering is normally only related to the activation of inspiration phases).

"Breathing device" as used herein means all known devices providing a breathable gas to a subject. This includes, inter alia, ventilators, respirators, anaesthetic machines and resuscitation devices.

State of the art breathing devices have a triggering functionality based on the gas parameters flow and pressure.

A flow triggering system is known from European Application 0 459 647, which discloses a breathing ventilator where a predetermined rate of flow of gas is delivered toward a patient. Changes in the rate of flow are measured and a breath support is triggered when the change in the rate of flow exceeds a threshold value (trigger level).

A pressure triggering system is known from U.S. Pat. No. 4,050,458 wherein pressure is measured and is analyzed with respect to the change of sign of a differentiated pressure signal. When a change occurs, an assisted inspiration phase can be started. In order to avoid self-triggering due to naturally occurring variations in pressure, the presence of a predetermined drop in pressure can be an additional requirement for triggering the inspiration phase.

Although these systems normally operate satisfactorily, there will be a delay time from the actual onset of a spontaneous inhalation attempt (originating in the respiratory center of the brain) until triggering actually occurs. This delay time may be more than 200 ms. Part of this is due to the transit time of the nerve signal and the response time of respiratory muscles, which have to start working before a change in pressure and flow can occur. The primary part of the delay, however, is due to the fact that triggering levels are set high enough to avoid any risk of self-triggering (i.e. the device being triggered to start an inspiration phase when there is no attempt made by the patient). It thus takes time before the effects of an inhalation reach the trigger requirement and start an inspiration phase.

This delay time is also present for variants of the flow and pressure trigger systems, such as volume trigger systems.

One attempt to avoid or reduce the delay time is disclosed in U.S. Pat. No. 5,373,842, wherein a pressure trigger system utilizes flow measurements on a bias flow to change the required trigger pressure level.

Although this result is a more stable trigger system with shorter response time, some of the delay time nevertheless remains.

Other known trigger systems use other parameters such as impedance across the chest disclosed in European Application 0 324 275, nerve signals as disclosed in PCT Application WO 00/00245 and muscle (myoelectric) signals as disclosed in PCT Application WO 99/43374.

The first of these essentially have the same delay times as the flow/pressure related triggering parameters, since the impedance will not change until the lungs start changing due to muscle activity. Here, also, thresholds must be set to avoid self-triggering from other impedance sources.

The latter two have less delay, but are not ideal in all situations. Muscle detection, for instance, normally relates to myoelectrical signals in the diaphragm. As stated in PCT Application WO 99/43374, however, inhalations can start with other muscle groups. Measuring activity in all muscles related to respiration is not realistic. A solution to this problem is suggested in PCT Application WO 99/43374, namely to have a separate flow or pressure trigger system operating in parallel and use a first come, first serve trigger operation. The delay time then remains for the flow/pressure trigger system (as well as for the muscle trigger).

It should also be noted that all systems triggering on excitable cell signals (nerves and muscles) are at risk of self-triggering unless a sufficiently high threshold for the triggering is set.

SUMMARY OF THE INVENTION

It is an object of the invention to provide a method that improves the trigger methods described above.

It is a further object of the invention to provide a breathing device having improved trigger features with respect to known triggering systems.

This object is achieved in accordance with the invention in a method wherein an excitable cell detector is used to obtain an excitable cell signal from a subject connected to the breathing device, and wherein the excitable cell signal is used to generate a respiration indicator signal which is, in turn, employed to adapt the trigger requirement.

The inventive triggering method is essentially based on a state of the art triggering method utilizing flow and/or pressure. The improvement lies in utilizing excitable cell signals related to respiration for adapting the trigger requirements for the flow and/or pressure trigger method.

Excitable cells are divided into two groups in humans, nerve cells and muscle cells. Excitable cells related to respiration thus include all nerves and muscles that take part in respiratory activity.

A preferred way of adapting the trigger requirement in relation to flow and/or pressure trigger methods is to adjust the trigger level based on the excitable cell signal. Since the excitable cell signal is indicative of a commencing breath, the risk of self-triggering is in practice quite insignificant and the trigger level therefore can be set to much higher sensitivity than is possible in the "pure" flow and/or pressure trigger method.

Another preferred way of adapting the trigger requirement in relation to flow and/or pressure trigger methods is to adjust or create a window in which triggering is enabled. Here, a constant high sensitivity can be set for the trigger level. Only when the excitable cell signal so indicates, will a triggering be allowed to result in the onset of an inspiration (or expiration) phase.

A combination of these two is of course possible. For instance, a certain level in the excitable cell signal (which could be lower than the trigger threshold for known systems using only such signals for triggering) starts a window in which triggering can take place. As the signal level increases (as the case is if inspirations are concerned) the flow and/or pressure trigger level will be changed toward higher sensitivity. This makes it possible to use a higher sensitivity and yet minimize the risk of self-triggering due to signal disturbances.

It should be noted that the prior art devices described above are mainly concerned with triggering of inspiration phases. The method according to the invention is, however, not limited to inspiration phases. It is also usable for triggering expiration phases.

Expiration phase triggering is often based on measured maximum pressure/flow levels during the actual breath. Ending an inspiration could e.g. be made when measured flow drops below a certain percentage of maximum flow. In the method according to the invention, the percentage is one specific trigger requirement that can be adapted by utilizing excitable cell signals.

In order to cover all patient types, the method can be further improved by further adaptation of the trigger requirement. One such further adaptation is the use of the known flow dependent pressure trigger system disclosed in U.S. Pat. No. 5,373,842, mentioned above.

A pressure dependent flow control also can be used in addition to the adaptation made on basis of the excitable cell signal. Particularly in view of progress in the development of extremely small and accurate pressure sensor, it has now become realizable to carry out pressure measurements within the lungs. Pressure measurements have thus become more reliable and usable.

The above object is also achieved in a breathing device wherein a first respiration indicator signal is obtained dependent on at least one of flow and pressure in a breathing gas circuit connected to a patient, wherein this first respirator indicator signal is compared to a trigger requirement, wherein a second respiration indicator signal is obtained from a signal measured by an excitable cell signal detector, and wherein this second respiration indicator signal is used to adapt the triggering requirement.

Here, the breathing device can essentially be based on a state of the art device, which is then equipped or connected to an excitable cell signal detector for detecting excitable cell signals and further equipped or modified to carry out necessary calculations and adaptations corresponding to that disclosed above in relation to the method.

Essentially any known prior art device for detecting excitable cell signals (and extracting/converting/calculating respiratory related information therefrom) can be used in connection with the present inventive breathing device. In particular, any known device which uses excitable cell signal information for determining the onset of an inhalation can be used in connection with the present breathing device.

DESCRIPTION OF THE PREFERRED EMBODIMENTS

Figure 1:
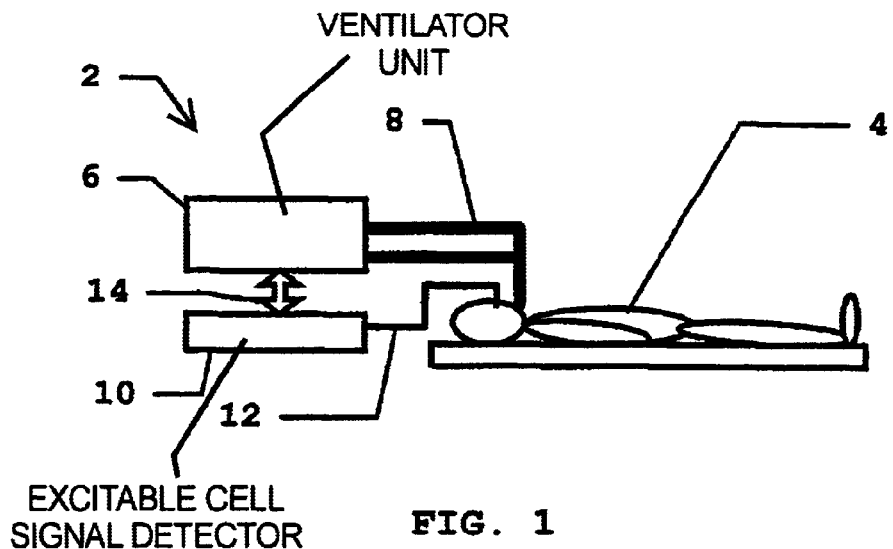
FIG. 1 shows a first embodiment of a breathing device according to the invention.

A breathing device 2 according to the invention is shown in FIG. 1. The breathing device 2 has in this embodiment a ventilator unit 6 connected to a patient 4 for delivering breathing gas to and removing breathing gas from the patient 4. Connection is in this case illustrated with a conventional tubing system 8 that can be connected to the patient via a tracheal tube, tracheotomy tube, face mask, etc.

Also connected to the patient 4 is an excitable cell signal detector 10, in this embodiment an esophageal diaphragm electromyography detector. The excitable cell signal detector 10 is connected to the patient 4 via a catheter lead 12 and can communicate with the other parts of the breathing device via a communication link 14.

Figure 3:
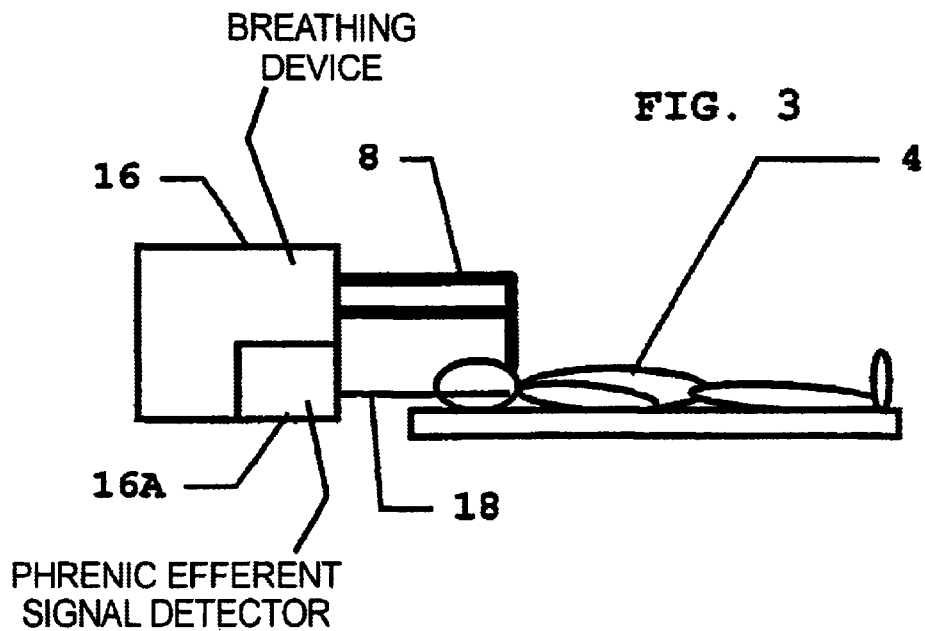
FIG. 3 shows a second embodiment of a breathing device according to the invention.

Another embodiment of the breathing device is shown in FIG. 3. Here the breathing device 16 includes all parts within the same enclosure. As with the breathing device 2, a conventional tubing system 6 connects the breathing device 16 to a patient 4.

In this second embodiment, the excitable cell signal detector is a phrenic efferent signal detector 16A. The phrenic efferent signal detector 16A is connected to the phrenic nerve on the patient 4 as indicated by the sensor line 18.

Figure 2:
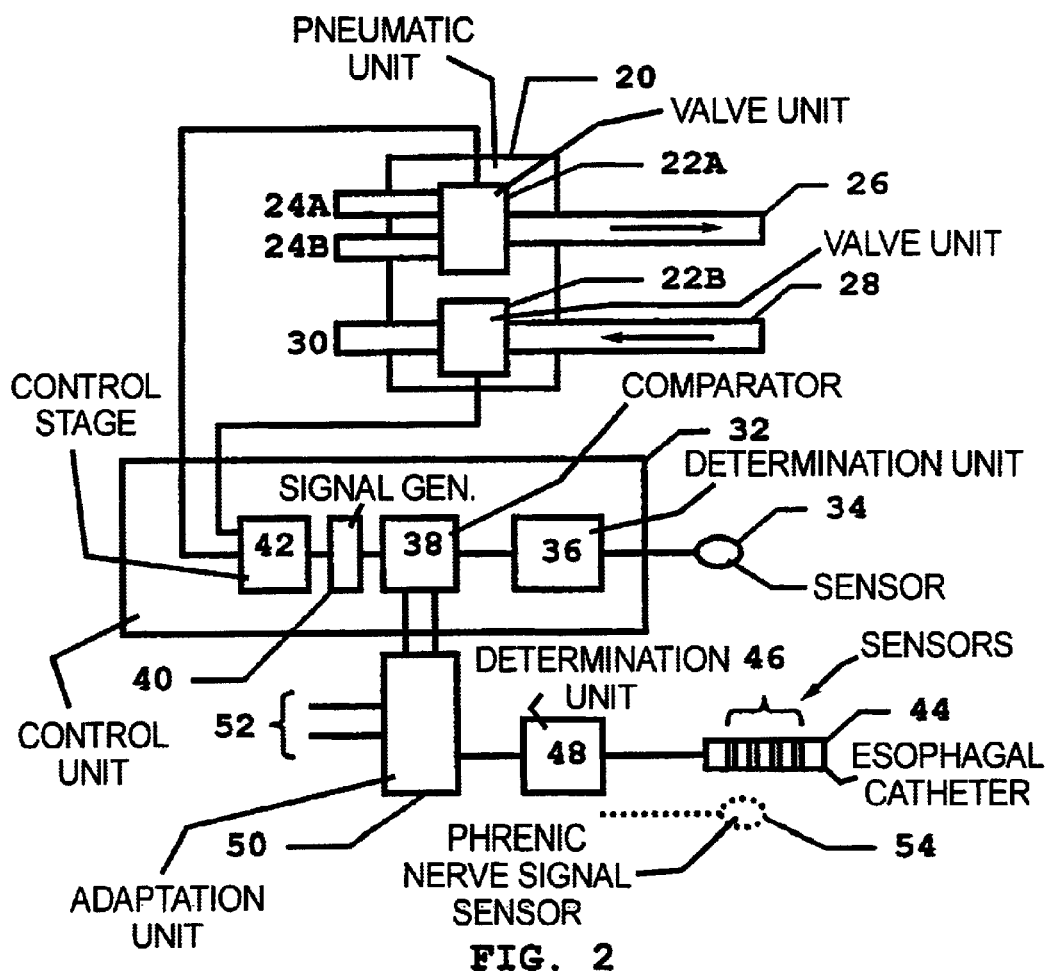
FIG. 2 shows some of the elements of the breathing device according to the invention in more detail.

A more detailed embodiment of the breathing apparatus 2 (or 16) is shown in FIG. 2. Parts that are different between the embodiments 2 and 16 are shown in broken lines. The detailed embodiment in FIG. 2 only shows the elements that are relevant for understanding the operation of the breathing device in relation to the inventive method.

A pneumatic unit 20 regulates flow of gases to and from a patient (not shown) by means of a first valve unit 22A and a second valve unit 22B. Gases that are mixed to form a breathing gas are supplied via a first gas inlet 24A and a second gas inlet 24B. The gases are proportioned and mixed in the first valve unit 20A. Additional gas inlets can be included if further gases are to be mixed to the breathing gas. The breathing gas is supplied toward the patient via an inspiration tube 26 and from the patient via an expiration tube 28. The second valve unit 20B controls the outflow of breathing gas from the patient. An evacuation 30 discharges the gas.

The pneumatic unit 20 is controlled by a control unit 32. In this case, only the operation of the control unit 32 in relation to triggering of respiration phases is discussed. Actual control of the pneumatic unit 20 to provide specific flows and pressures for supporting respiration is well known in prior art systems.

A sensor 34 measures pressure. The pressure signal is used by a first determination unit 36 to determine a first respiration indication signal (e.g. pressure within the patient's lungs).

The first respiration indication signal is supplied to a comparator 38 for comparison with a trigger level. Basically, the comparator 38 can be formed by circuitry (if made in hardware) or programming (if made in software) enabling it to compare the first respiration indication signal with an inspiration trigger level during expiration phases and an expiration trigger level during inspiration phases. As an example, the following relate to comparison with an inspiration trigger level.

In a prior art pressure trigger device, first respiration indication signal input into the comparator 38 would eventually reach the inspiration trigger level. A signal generator 40 generates a trigger signal which is utilized by a further control stage 42 in the control unit 32 to start an inspiration phase by controlling the first valve unit 20A in the pneumatic unit 20.

In a similar manner the second valve unit 20B can be controlled to start an expiration phase.

According to the present invention, the triggering requirement is adapted by a second respiration indication signal, derived from detection of excitable cell signals.

Excitable cells, i.e. nerves or muscles, generate myoelectrical signals that can be detected and treated to derive information. In this instance, information related to respiration is of interest. It is thus signals from nerves and/or muscles involved in the respiration that should be detected.

The muscles involved in breathing are essentially the diaphragm and the scalene and external intercostal muscles during inspiration and abdominal and internal intercostal muscles during expiration. Of these, the diaphragm has the greatest importance and is therefore of greatest interest in detecting muscle signals. As noted in the prior art discussion, it is known to detect diaphragm myoelectric signals by using an esophageal catheter 44 on which a plurality of sensors 46 is applied to detect the signals. In a second determination unit 48 the signals can be filtered, amplified or treated in any known way to create a second respiration indication signal.

The second respiration indication signal is transferred to an adaptation unit 50. The adaptation unit 50 is connected to the comparator 38. Trigger levels (either set by an operator or fixed for different applications of the breathing device) are linked to the comparator 38 via the adaptation unit 50.

The adaptation unit 50 adapts the trigger requirement so as to achieve a more reliable, sensitive and stable triggering of respiration phases.

One way of adapting the trigger requirement is to adjust the trigger level in dependency of the second respiration indication signal. For inspiration triggering, this means (in the present embodiment) that the trigger level itself is brought closer to the actual pressure within the patient (the first respiration indication signal). The comparator 38 and signal generator 40 therefore will respond earlier to an inspiration attempt from the patient than would be possible with prior art pressure trigger systems.

Another way of adapting the trigger requirement is to maintain a high sensitivity on the pressure trigger (i.e. trigger level being close actual pressure). To avoid self-triggering, the adaptation resides in inhibiting triggering as long as the second respiration indication signal is too low. As the second respiration indication signal reaches a certain level, triggering on pressure is enabled. With this approach, it becomes unnecessary for the operator to set trigger requirements.

A third way of adapting the trigger requirement is to combine the two previous. In short, triggering could be enabled at a first level of the second respiration indication signal and the trigger level could then be changed towards the value of first respiration indication signal.

The same is possible in relation to nerve signals. The phrenic nerve is one example of a nerve involved in respiration. The signals along this nerve can be detected by a sensor 54 (indicated in broken lines). Signal treatment differs somewhat from what is done with muscle signals, but there are known ways of extracting the information relevant to respiration from the nerve signal.

Figure 4:
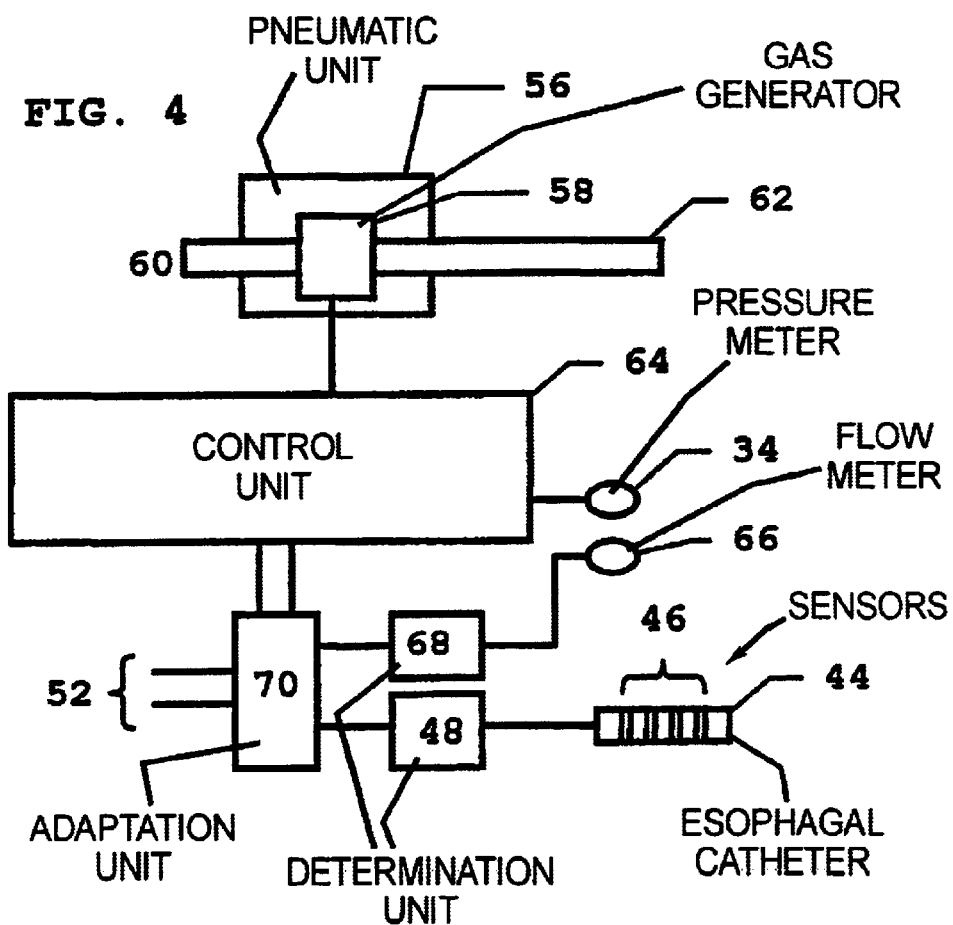
FIG. 4 shows a third embodiment of a breathing device according to the invention.

Another detailed embodiment of the breathing apparatus according to the invention is shown in FIG. 4. Elements that can be identical with elements in FIG. 2 have the same designation numbers.

In this embodiment, the pneumatic unit 56 includes a gas generator 58, such a compressor or a fan. The gas generator 58 takes in air via an inlet 60 and regulates a breathing gas flow into a breathing tube 62 according to control signals from a control unit 64. The breathing tube 62 can e.g. be connected to a patient via a breathing mask with separate outlet for expired gas (not shown).

A pressure meter 34 measures pressure and transfers the pressure signal to the control unit 64. In the control unit a software program receives the pressure signal, processes it and compares it with a trigger level. Pressure is thus a first respiration indication signal. An esophageal catheter 44 on which a plurality of sensors 46 is applied to detect the signals from the diaphragm after being introduced into the esophagus. These signals are transferred to a determination unit 48 which determines a second respiration indication signal. The second respiration indication signal is transferred to an adaptation unit 70 to be used for adapting the trigger requirement. The adapting can be made in any of the ways discussed above in relation to FIG. 2. Trigger levels are input via numeral 52.

To further adapt the trigger requirement, a flow meter 66 is used to measure flow of gas in breathing tube 62. The flow signal is transferred to a determination unit for determining a third respiration indication signal. The third respiration indication signal is sent to the adaptation unit 70 for further or combined adaptation of the trigger requirement.

One way of making a combined adaptation, is to use the second respiration indication signal for enabling triggering and the third respiration indication signal for increasing sensitivity of the pressure trigger level.

Another way is to combine the second respiration indication signal and third respiration indication signal for altering the trigger level.

A combination of the two is of course also possible.

Combinations of the shown embodiments are possible. For instance, the pneumatic unit 20 in FIG. 2 can be replaced with the pneumatic unit 56 in FIG. 4 and vice versa (with appropriate changes in respective control unit 32, 64).

Further modifications can also be done by adding, combining or changing elements in the prior art with shown embodiments in this description. For example, the pneumatic unit can basically be any known pneumatic unit usable in a breathing device. The same is valid for the tubing system. For example, anaesthetic elements have not been shown in the embodiments, but can of course be used in the same manner.

It is not necessary to measure diaphragm myoelectrical signals via an oesophageal catheter. Other means of obtaining these signals can also be used. Similarly, myoelectrical signals from other respiratory muscles can be used in the same way.

The same is of course valid for the nerve signals, which need not be obtained from the phrenic nerve.

The basic inventive concept of the invention is the use of excitable cell signals to modify or adapt the trigger requirement for respiration phases, either as a method or implemented in a breathing device.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for adaptively triggering respiration phases in a breathing device, comprising the steps of:
    providing exclusively pneumatic breathing assistance to a patient via a tubing system connected to a breathing circuit in which the patient participates;
    determining a first respiration indicator signal in said breathing gas circuit based on at least one parameter selected from the group consisting of flow and pressure in said breathing gas circuit;
    comparing said first respiration indicator signal with a trigger requirement in said exclusively pneumatic breathing assistance;

generating a trigger signal to trigger a respiratory phase in said exclusively pneumatic breathing assistance when said first respiration indicator signal satisfies said trigger requirement;

measuring an excitable cell signal related to respiration in said patient participating in said breathing gas circuit;

determining a second respiration indicator signal based on the measured excitable cell signal; and adapting said trigger requirement dependent on said second respiration indicator signal.

2. A method as claimed in claim 1 wherein said trigger requirement is trigger sensitivity, and wherein the step of adapting said trigger requirement comprises increasing said trigger sensitivity relative to said first respiration indicator signal when said second respiration indicator signal indicates commencement of a natural change of respiratory phase.

3. A method as claimed in claim 1 wherein said trigger requirement is trigger enablement, and wherein the step of adapting the trigger requirement comprises enabling triggering only when said second respiration indicator signal indicates commencement of a natural change of respiratory phase.

4. A method as claimed in claim 1 wherein the step of measuring an excitable cell signal comprises measuring a phrenic efferent discharge.

5. A method as claimed in claim 1 wherein the step of measuring an excitable cell signal comprises measuring a muscle signal.

6. A method as claimed in claim 5 wherein the step of measuring a muscle cell signal comprises measuring a diaphragm electromyography signal.

7. A method as claimed in claim 1 wherein the step of determining a first respiration indicator signal comprises determining said first respiration signal based on only one of said parameters selected from the group consisting of flow and pressure, and comprising the additional steps of:

determining a third respiration indicator signal based on the other of the parameter selected from the group consisting of flow and pressure; and additionally adapting said trigger requirement dependent on said third respiration indicator signal.

8. A breathing device comprising:

a tubing system adapted for communication with a subject;

a pneumatic unit in communication with said tubing system for regulating a flow of breathing gas in said tubing system for providing exclusively pneumatic breathing assistance to the subject;

a sensor system in communication with said tubing system including at least one meter selected from the group consisting of a flow meter for measuring flow of said breathing gas in said tubing system and a pressure meter for measuring a pressure of said breathing gas in said tubing system;

a control unit connected to said pneumatic unit for controlling said pneumatic unit, said control unit comprising a first determination unit connected to said sensor system for receiving a measurement signal from said sensor system representing at least one parameter and for determining a first respiration indication signal based on said at least one parameter, a comparator connected to said first determination unit for receiving said first respiration indication signal therefrom and for comparing said first respiration indication signal with a trigger requirement in said exclusively pneumatic breathing assistance, said comparator generating a comparator output dependent on whether said trigger requirement is satisfied by said first respiration indication signal, and a signal generator supplied with said comparator output for generating a trigger signal for controlling triggering of a respiratory phase in said exclusively pneumatic breathing assistance dependent on said comparator output;

an excitable cell detector adapted for detecting excitable cell signals related to respiration by said subject;

a second determination unit supplied with said excitable cell signals for determining a second respiration indicator signal based on said excitable cell signals; and an adaptation unit supplied with said second respiration indicator and connected to said comparator, for adapting said trigger requirement dependent on said second respiration indicator signal and supplying said trigger requirement to said comparator.

9. A breathing device as claimed in claim 8 wherein said trigger requirement is trigger sensitivity, and wherein said adaptation unit increases the trigger sensitivity relative to said first respiration indicator signal when said second respiration indicator signal indicates commencement of a natural change of respiratory phase.

10. A breathing device as claimed in claim 8 wherein said trigger requirement is trigger enablement, and wherein said adaptation unit adapts said trigger requirement to enable triggering only when said second respiration indicator signal indicates commencement of a natural change of respiratory phase.

11. A breathing device as claimed in claim 8 wherein said excitable cell signal detector comprises a nerve signal sensor.

12. A breathing device as claimed in claim 11 wherein said nerve signal sensor comprises a phrenic efferent signal sensor.

13. A breathing device as claimed in claim 8 wherein said excitable cell signal detector comprises a muscle signal sensor.

14. A breathing device as claimed in claim 13 wherein said muscle signal sensor comprises a diaphragm electromyography sensor.

15. A breathing device as claimed in claim 14 wherein said diaphragm electromyography sensor comprises an esophageal catheter having an array of sensing electrodes.

* * * * *